(12) United States Patent
Shalon et al.

(10) Patent No.: US 8,323,300 B2
(45) Date of Patent: Dec. 4, 2012

(54) TISSUE ANCHORABLE DEVICES

(75) Inventors: Tidhar Shalon, Tel-Aviv (IL); Guy Kotlizky, Kfar-Shemaryahu (IL)

(73) Assignee: SVIP 8 LLC, Palo Alto, CA (US)

( * ) Notice: Subject to any disclaimer, the term of this patent is extended or adjusted under 35 U.S.C. 154(b) by 311 days.

(21) Appl. No.: 12/451,850

(22) PCT Filed: Jun. 3, 2008

(86) PCT No.: PCT/IL2008/000749
§ 371 (c)(1),
(2), (4) Date: Dec. 3, 2009

(87) PCT Pub. No.: WO2008/149347
PCT Pub. Date: Dec. 11, 2008

(65) Prior Publication Data
US 2010/0137891 A1    Jun. 3, 2010

Related U.S. Application Data

(60) Provisional application No. 60/924,867, filed on Jun. 4, 2007.

(51) Int. Cl.
*A61B 17/00* (2006.01)
(52) U.S. Cl. .................. 606/153; 606/139; 606/151
(58) Field of Classification Search .................. 606/153, 606/151, 157, 139, 41; 623/23.68, 23.7; 607/40
See application file for complete search history.

(56) References Cited

U.S. PATENT DOCUMENTS

| | | | |
|---|---|---|---|
| 4,878,905 A | 11/1989 | Blass | |
| 5,156,641 A | 10/1992 | White | |
| 5,185,005 A | 2/1993 | Ballantyne | |
| 5,234,454 A | 8/1993 | Bangs | |
| 6,231,589 B1 | 5/2001 | Wessman et al. | |
| 6,254,570 B1 | 7/2001 | Rutner et al. | |
| 6,264,700 B1 * | 7/2001 | Kilcoyne et al. | 623/23.68 |
| 6,746,460 B2 | 6/2004 | Gannoe et al. | |
| 6,754,536 B2 | 6/2004 | Swoyer et al. | |
| 6,971,395 B2 * | 12/2005 | Edwards et al. | 128/898 |
| 7,316,716 B2 * | 1/2008 | Egan | 623/23.65 |
| 7,430,450 B2 | 9/2008 | Imran | |
| 2002/0103424 A1 | 8/2002 | Swoyer et al. | |
| 2003/0208183 A1 | 11/2003 | Whalen et al. | |
| 2004/0030347 A1 | 2/2004 | Gannoe et al. | |
| 2004/0185083 A1 | 9/2004 | Dionne et al. | |
| 2005/0177181 A1 | 8/2005 | Kagan et al. | |
| 2005/0283246 A1 | 12/2005 | Cauthen, III et al. | |
| 2006/0020278 A1 | 1/2006 | Burnett et al. | |

(Continued)

FOREIGN PATENT DOCUMENTS

WO    WO 2005/009288    2/2005

(Continued)

OTHER PUBLICATIONS

Response Dated Mar. 24, 2011 to Office Action Dated Jan. 12, 2011 From the Israel Patent Office Re. Application No. 197198.

(Continued)

*Primary Examiner* — Vy Q Bui

(57) ABSTRACT

A device for treating GERD is provided. The device includes a device body capable of at least partially preventing reflux of stomach content to the esophagus while enabling flow of esophageal content around said device body and into the stomach.

4 Claims, 6 Drawing Sheets

U.S. PATENT DOCUMENTS

| | | |
|---|---|---|
| 2006/0079944 A1 | 4/2006 | Imran |
| 2006/0282127 A1 | 12/2006 | Zealear |
| 2007/0021736 A1 | 1/2007 | Johnson |
| 2007/0080188 A1 | 4/2007 | Spence et al. |
| 2007/0162085 A1 | 7/2007 | DiLorenzo |
| 2007/0246052 A1 | 10/2007 | Hegde et al. |
| 2007/0250020 A1 | 10/2007 | Kim et al. |
| 2008/0004598 A1 | 1/2008 | Gilbert |
| 2008/0091247 A1 | 4/2008 | Muller et al. |
| 2008/0221599 A1 | 9/2008 | Starksen |
| 2009/0187230 A1 | 7/2009 | DiLorenzo |
| 2009/0247992 A1 | 10/2009 | Shalon et al. |
| 2010/0305656 A1 | 12/2010 | Imran et al. |
| 2012/0165855 A1 | 6/2012 | Shalon et al. |

FOREIGN PATENT DOCUMENTS

| | | |
|---|---|---|
| WO | WO 2008/003097 | 1/2008 |
| WO | WO 2008/023374 | 2/2008 |
| WO | WO 2008/132745 | 11/2008 |
| WO | WO 2008/149347 | 12/2008 |
| WO | WO 2009/072115 | 6/2009 |
| WO | WO 2009/147670 | 12/2009 |

OTHER PUBLICATIONS

Official Action Dated Apr. 18, 2011 From the US Patent and Trademark Office Re. U.S. Appl. No. 12/310,359.

Supplementary European Search Report and the European Search Opinion Dated Oct. 31, 2011 From the European Patent Office Re. Application No. 09758014.6.

Communication Pursuant to Article 70(2) and 70a(2) EPC Dated Nov. 17, 2011 From the European Patent Office Re. Application No. 0978014.6.

Notice of Allowance Dated Nov. 18, 2011 From the US Patent and Trademark Office Re. U.S. Appl. No. 12/310,359.

International Preliminary Report on Patentability Dated Dec. 16, 2010 From the International Bureau of WIPO Re. Application No. PCT/IL2009/000551.

International Preliminary Report on Patentability Dated Apr. 9, 2009 From the International Bureau of WIPO Re.: Application No. PCT/IL2007/001047.

International Search Report and the Written Opinion Dated Oct. 13, 2009 From the International Searching Authority Re.: Application No. PCT/IL09/00551.

International Search Report Dated Jul. 3, 2008 From the International Searching Authority Re.: Application No. PCT/IL07/01047.

International Search Report Dated Nov. 13, 2008 From the International Searching Authority Re.: Application No. PCT/IL08/00749.

Written Opinion Dated Jul. 3, 2008 From the International Searching Authority Re.: Application No. PCT/IL07/01047.

Written Opinion Dated Nov. 13, 2008 From the International Searching Authority Re.: Application No. PCT/IL08/00749.

International Preliminary Report on Patentability Dated Jan. 28, 2010 From the International Bureau of WIPO Re.: Application No. PCT/IL2008/000749.

Response Dated Jun. 21, 2011 to Official Action of Apr. 18, 2011 From the US Patent and Trademark Office Re. U.S. Appl. No. 12/310,359.

Examiner's Report Dated Mar. 21, 2012 From the Australian Government, IP Australia Re. Application No. 2007287201.

English Summary of Notice of Rejection Dated May 22, 2012 From the Japanese Patent Office Re. Application No. 2009-525171.

Office Action Dated Mar. 25, 2012 From the Israel Patent Office Re. Application No. 197198 and Its Translation Into English.

* cited by examiner

TISSUE ANCHORABLE DEVICES

RELATED APPLICATIONS

This application is a National Phase Application of PCT Patent Application No. PCT/IL2008/000749 having International Filing Date of Jun. 3, 2008, which claims priority from U.S. Provisional Patent Application No. 60/924,867, filed on Jun. 4, 2007. The contents of the above Application are all incorporated herein by reference.

FIELD AND BACKGROUND OF THE INVENTION

The present invention relates to tissue anchored devices and systems. In particular, the present invention relates to tissue anchored devices which can be used to treat GI related disorders such as gastroesophageal reflux disorder (GERD).

Tissue anchoring is employed in a variety of gastrointestinal procedures, such as stomach volume reduction, placement of stomach-anchored devices such as electrodes and sphincter repair or functional augmentation [e.g. gastroesophageal reflux disorder (GERD) treatment].

One inherent limitation of current anchorable designs is lack of compliance to forces subjected thereupon. In the GI tract, anchored devices are exposed to constant tissue movement and to a harsh environment as well as flow of liquids, making long term anchoring very difficult with presently available anchor designs.

While reducing the present invention to practice, the present inventors have devised a GERD treatment approach which overcomes the limitations of prior art devices.

SUMMARY OF THE INVENTION

According to one aspect of the present invention there is provided a device for reducing reflux comprising a device body and an anchor for anchoring the device body within or below the esophagus, wherein the device is configured for: (i) at least partially preventing reflux of stomach content into the esophagus; and (ii) enabling flow of esophageal content around the device body and into the stomach.

According to further features in preferred embodiments of the invention described below, the device body is shaped as a ball, an ellipsoid, a flat sheet, a contoured sheet, or a cone.

According to still further features in the described preferred embodiments the device body is anchored at a single side of an esophageal lumen or LES.

According to still further features in the described preferred embodiments the device body is anchored to an esophageal or stomach tissue using at least one tether.

According to still further features in the described preferred embodiments the at least one tether is an elastic tether.

According to still further features in the described preferred embodiments the at least one tether is fabricated from silicone.

According to still further features in the described preferred embodiments the device body is fabricated from silicone.

According to still further features in the described preferred embodiments the device is configured such that the device body is capable of changing position relative to the LES.

According to still further features in the described preferred embodiments the device body enables at least partial natural closure of the LES.

According to another aspect of the present invention there is provided a method of reducing reflux comprising anchoring a device having a device body to tissue of a subject in need the device body configured for: (i) at least partially preventing reflux of stomach content into the esophagus; and (ii) enabling flow of esophageal content around the device body and into the stomach.

According to still further features in the described preferred embodiments the device is configured such that the device body is capable of changing position relative to the LES.

According to still further features in the described preferred embodiments the anchoring is effected by tethering the device body to esophageal or stomach tissue.

According to still further features in the described preferred embodiments the anchoring is effected by attaching the device body in a region of the LES.

According to still further features in the described preferred embodiments the anchoring is effected by attaching the device body against esophageal and/or stomach tissue.

According to yet another aspect of the present invention there is provided a tissue anchor comprising a tissue anchoring element attached to a tether having elastic properties.

According to still further features in the described preferred embodiments the tether is capable of elastically increasing in length by at least 25%.

According to still further features in the described preferred embodiments the tether is capable of elastically increasing in length by at least 50%.

According to still further features in the described preferred embodiments the tissue anchoring element is anchorable against a tissue.

According to still further features in the described preferred embodiments the tissue anchoring element is anchorable within a tissue.

According to still further features in the described preferred embodiments the tissue anchoring element is a t-bar element.

According to still further features in the described preferred embodiments at least a portion of the tether is fabricated from an elastic material.

According to still further features in the described preferred embodiments the at least a portion of the tether is fabricated from silicone.

According to still further features in the described preferred embodiments the tissue anchoring element is fabricated from a polymer.

According to still further features in the described preferred embodiments the tether comprises a tissue stop element along a length thereof.

According to still another aspect of the present invention there is provided an implantable device comprising a device body attached to at least one tissue anchor, the tissue anchor comprising a tissue anchoring element attached to a tether being fabricated from an elastic material.

The present invention successfully addresses the shortcomings of the presently known configurations by providing a simple anchor which can be used to anchor various devices to tissue. The present invention further provides devices suitable for treatment of obesity, GERD, sleep apnea or orthopedic disorders which are safe and easy to implant and remove while having minimum impact on the physiology or anatomy of implanted tissues.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
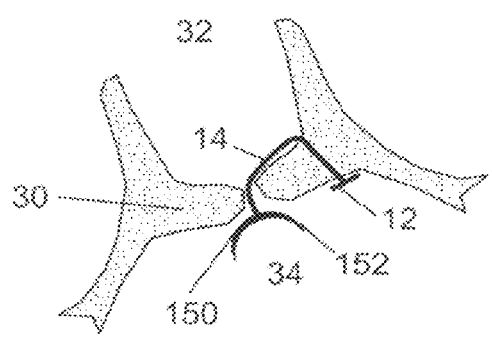
FIGS. 1a-h illustrate various embodiments of a GERD treatment device constructed in accordance with the teachings of the present invention.

The present invention is of devices and methods which can be used to treat acid reflux in a subject such as a human.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In a previously filed patent application, the present inventors have described novel approaches for treating obesity using stomach-anchorable satiety-inducing devices. Experimentation with various anchoring approaches and device configurations suitable for treatment of GERD have led to the formulation of the embodiments described herein.

GERD is a condition in which the esophagus becomes irritated or inflamed because of acid or other fluids such as bile or water backing up from the stomach into the esophagus (reflux).

Although it has been shown that abnormal functioning of the lower esophageal sphincter (LES) which is at the junction of the esophagus and stomach leads to GERD, the underlying cause for GERD is not always apparent. Up to 25% of patients with GERD do not respond to proton pump inhibitor (PPI) drugs that are very effective at lowering stomach acid production, indicating that it is not always acid reflux that causes GERD.

In addition to a malfunctioning LES, other factors such as obesity, slow emptying of stomach content, weak muscular contractions in the esophagus, exercise, pregnancy, smoking, certain hormones, many foods, and some medications can aggravate this disorder.

Approaches for treating GERD include lifestyle changes, medication and endoscopic procedures. Proton pump inhibitors (PPIs) represent the mainstay of therapy for patients with non-erosive reflux disease (NERD), and while modern technologic advances in endoscopic procedures have improved the efficacy of endoluminal GERD therapy, currently practiced approaches are still limited in as far as long term efficacy. Many of the endoscopic suturing devices (such as Bard's Endocinch™) try to use inelastic sutures to modify the natural anatomy of the LES. The sutures end up eroding through the tissue which is constantly working against the sutures, and therefore the procedure loses its effectiveness over time.

Although numerous devices for treating GERD have been described in the patent literature (see, for example, U.S. Pat. Nos. 4,846,836; 5,314,473; 5,861,036 and 6,264,700), such devices are designed to replace rather than augment the function of the LES and as such are bulky and intrusive and thus may lead to migration, erosion, dysphagia as well as other morbidities. Furthermore, many endoscopic fundiplication techniques exist (for example NDO™ surgical, Esophyx™ from EndoGastric Solutions Inc, and Medigus™), but these are quite complicated procedures and expensive devices requiring significant training, lengthy anesthesia and operating room times, and the expertise of a surgeon in addition to the endoscopist for implementation. Furthermore these techniques are generally not reversible, which is a desired feature for patients.

The present inventors propose that effective GERD treatment can be accomplished without altering the anatomy of the LES or surrounding regions of tissue.

A device designed for long term treatment of GERD must take into consideration the following:

it should minimally impact normal LES anatomy and function;

(ii) it should allow relatively smooth passage of esophageal content (e.g food and liquids) into the stomach without causing dysphagia;

(iii) it should be easy to position and anchor in the esophagus/stomach via endoscopic procedure while minimizing risk of damage to adjacent tissues;

(iv) it should function in minimizing flow of stomach content to the esophagus (e.g. reflux) regardless of the patient position (lying/standing), reflux composition and reflux quantity; and (v) it should allow passage of gas from stomach to esophagus and either prevent or enable vomiting, depending on physician or patient preference; and (vi) it should be reversible to the extent possible A device having features which follow the guidelines above can be constructed by attaching a device body functional in at least partially blocking the LES to the wall of the stomach, esophagus or LES. As is further described hereinunder, such attachment can be facilitated by elastic or non-elastic anchoring approaches.

Studies have shown that at least in some cases, incomplete closure of the LES leads to the formation of an LES fluid nozzle (1-2 mm in diameter) which generates a fluid jet directed at the esophageal walls under reflux [McMahon et al. World J Gastroenterol 2007 Mar. 7; 13(9): 1360-1364]. Other studies indicate a bigger opening of the LES during GERD or NERD.

The present inventors postulate that partially or fully blocking the flow of fluid up through the LES opening via a one way "flap valve" type device positioned at or near the LES would be enough to prevent reflux into the esophagus. Thus, the present device can be designed for completely (and intermittently) blocking the LES region or for blocking only the transient orifice formed in the LES. Preferably, the present device is designed such that partial or complete blockage of the LES occurs only during reflux episodes in the esophageal direction. This can be achieved by suspending the present device in or under the LES in a position which lies in the path of reflux, such that a reflux episode pushes the device body against the lower or lateral LES surfaces, thereby blocking it and preventing reflux from passing into the esophagus.

Alternatively, the device of the present invention can elastically bulk and therefore block the orifice formed by the LES by residing in the lumen and being capable of elastic deformation in the radial direction. In the embodiment where the device is a hollow elastic cone suspended in the esophagus at the sealing point of the LES, peristaltic waves will collapse the cone and minimize its profile thereby minimizing the forces trying to detach the device. Likewise, food passing down through the esophagus can collapse the cone and pass easily into the stomach without causing dysphagia, while reflux due to higher inter-stomach pressure will expand the cone outwards and therefore increase the sealing pressure of the device against the LES surface, thereby blocking reflux.

In a further embodiment, the device of the present invention can have a generally cylindrical device body that is suspended like a "boat bumper" in the lumen right above the LES and terminates right under it, with or without a rim or disc at its distal tip and with or without a lower anchoring point. Such a cylindrical device body, anywhere from 1 to 10 mm in diameter acts as an internal bulking of the LES lumen by forming a mandrel around which the LES contracts to improve the seal against reflux, yet does not significantly interfere with the diameter of the lumen when the LES is open for the passage of a food bolus. Such device body can be of a prefixed size made from elastic material such as silicone or hollow (and filled as describe later in this application) to allow the proper volume of internal bulking to alleviate GERD.

The seal between the present device and the LES can be selective and thus allow natural passage of gas, during for example, burping and yet block passage of liquids. Such selectivity can be activated by pressure or the presence of liquid, for example, the device can seal and prevents passage of liquid to the esophagus under high pressure. Alternatively, if burping occurs at a higher pressure than the reflux, the device can seal at low pressure and only open during the high pressure episode of a burp. Likewise, under the tremendous forces of vomiting, the present device would be sized so that it will remain in position and yet allow vomit to escape, or alternatively the device will be small enough so that it can be pushed up into the esophagus and remain tethered against the side therein and not interfere with the passage of vomit. At the peristaltic wave, e.g. a swallowing saliva, drink of water or eating of food, the device would be pushed back into the stomach and resume its position of sealing the esophagus.

FIGS. 1a-h illustrate several embodiments of a device for treating GERD which is referred to herein as device 150. The lower esophageal sphincter (designated as LES 30), is shown in cross section and separates esophagus 32 from stomach 34.

FIG. 1a illustrates a device 150 having device body 152 configured as a flap, sheet, cone or dome having a surface area of 0.2-10 cm$^2$, preferably around 1 cm$^2$ to cover the LES opening, yet minimize drag forces trying to pull device body 152 from its anchored position and thereby causing erosion and eventual loss of device 150. Device body 152 can be constructed from a thin piece of silicone, latex rubber, polyamides (e.g. polyurethane—Tecoflex™), polyethylene, polypropylene, polyester, PEEK, Tefzel, PVDF, trifluoropropyl or phenyl modified dimethylpolysiloxane elastomer for improved acid resistance, or similar material having a thickness of 0.1-3 mm and Shore A value of 0-100. Device body 152 can be coated with an acid neutralizing material to prevent device body degradation or fabricated from an acid resistant material. Device 150 or just device body 152 can be coated with an antibacterial coating, such as Surfacine™ to reduce the likelihood of bacterial colonization or the formation of a biofilm on the device surface. Rigidity can be provided by support structures such as ribs in the form of radial spokes and/or a circumferential rim around device body 152. Device body 152 can be solid or porous (e.g. mesh-like) and hydrophobic or hydrophilic in nature. Although a collapsible dome or conical configuration is shown in FIG. 1a (designed to minimize drag forces on the food and liquid esophageal contents passing around device 150 into the stomach), other configurations are also envisaged (see FIGS. 1b-h). For example, device body 152 can be an inverted golf tee shape, a flat rectangular, round or oval sheet, or stacked sheets which is flat, or formed into conical or pyramidal structures. Device body 152 can be designed to assume a compressed state for delivery (e.g. deflated balloon, rolled up sheet, flattened cone, elongated hollow ball) and be deployed hydrostatically, mechanically, electrically or chemically following positioning of device 150. For example, device body 152 can be held in a compressed state via an acid or fluid labile structure (e.g. a compressive band or encapsulating body) which when exposed to stomach acid degrades to release device body 152 which then assumes the deployed expanded shape. Such a compressive structure can be fabricated from, for example, cellulose, gelatin, alginate, pectin and the like.

Device body 152 can be attached to one or more anchors depending on the site of anchoring and configuration of device body 152. For example, when anchored to the esophageal wall at or above the LES (further described below), device body 152 is attached to a single anchor; when anchored to the stomach wall (e.g. at the greater or lesser curvature regions) several anchors are attached to end of device body 152.

Single or at most dual point elastic anchoring is advantageous in that it allows for device body 152 to move a bit and not be in prolonged contact with any one region of the tissue, which could cause erosion or ulceration. A bit of freedom of motion, on the order of 1 mm to 4 cm due to a stretch of exposed tether between device body 152 and the tissue surface, or due to the elastic deformation of the tether itself ensures that device body is generally present at the anatomical location required for functioning. At the same time, any peristaltic motion or tissue deformation distributes the contact pressure of the device onto a larger tissue area which prevents erosion at any one given point on the tissue. Furthermore, an elastic tether can allow the device to elongate together with the passage of esophageal content or peristaltic wave until the wave passes, and then the device returns to its resting position due to relaxation of the elastic tether. Device body 152 can also be shaped to augment the curvature of the angle of His. Some cases of GERD are brought about by a change in the curvature of the angle of His which is thought to function in controlling reflux. Thus, device body 152 which is shaped to augment this region and is anchored to the stomach wall in the region abutting the tissue forming the angle of His can be used to control reflux. In an alternative embodiment, device body 152 can act as a ridge or gutter deflecting reflux fluids back down towards the stomach and away from the esophageal opening.

Device body 152 can also be configured as an elastic spiral which when stretched assumes a tether-like configuration and when relaxed assumes a bulkier, rod or flat sheet-like structure (e.g. similar to a telephone cord or a spirally cut orange peel). Such a device body 152 can be anchored at the LES and stretched to assume a tether/string configuration during passage of a peristaltic wave or food (i.e, when stretched by food passing through the LES) and relax to assume a sheet or ball configuration which can augment sealing at the LES.

Several anchor configurations can be utilized to anchor device body 152 to tissue at or around the LES.

Figure 2:
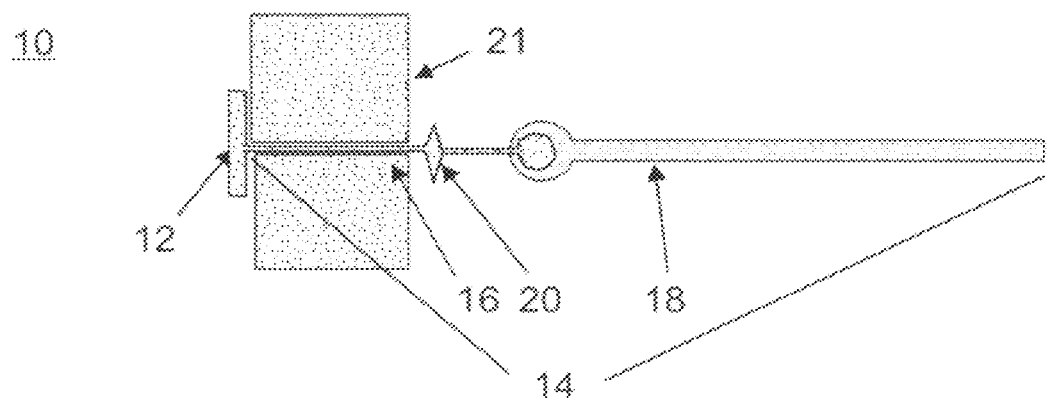
FIG. 2 illustrates one embodiment of an anchor designed in accordance with the teachings of the present invention.

FIG. 2 illustrates one embodiment of the anchor of the present invention, which is referred to herein as anchor 10. Anchor 10 can be an elastic or a non-elastic anchor.

Anchor 10 includes an anchoring element 12 (through-tissue t-bar configuration in this case), which is attached to tether 14. Although one tether is shown in FIG. 2, it will be appreciated that a configuration of anchor 10 in which anchoring element 12 is attached to several tethers 14 is also envisaged.

In the configuration depicted in FIG. 2, anchoring element 12 and a first portion 16 of tether 14 are co-molded from polypropylene and attached to a second portion 18 of tether 14 which can be fabricated from elastic or non-elastic materials; portion 18 can be molded over portion 16 or press-fit or glued thereto. Tether 14 is also provided with a stopper structure 20 which serves to limit backing up of anchor 10 following positioning thereof in tissue 21.

An elastic anchor 10 configuration of the present invention includes a tissue anchoring element which is attached to at least one tether 14 configured for elastic compliance. Human tissues are dynamic and the forces and strains generated by tissue movement can be large enough to cause non-compliant or non-elastic (e.g. polyester or polypropylene) sutures or tethers to cut through or rip out of tissue or erode surfaces such as mucosa. This is especially true if a non-compliant suture or tether attempt to constrain the normal motion of the tissue or is in a geometry that does not allow for relative motion between itself and the tissue. Therefore, single point compliant anchoring where the tissue can move along the length of the tether or alternatively elastic or compliant anchoring of the present device as is taught by the present invention is preferred as it does not constrain the tissue from its natural movement and thus minimizes the chances of anchor failure and tissue erosion.

Tissue anchoring element 12 can be any structure suitable for providing in or through-tissue anchoring capabilities. Examples include t-bar structures, barbs, coils (e.g. screw-in coils), pig-tail structures (e.g. anchoring elements which form coiled pig tail structures when relaxed and linearize when forcibly pulled), umbrellas, balls (expandable, static, hollow, solid or wire) screws or any other structures capable of residing in or against a tissue and opposing a force applied thereto in one or more directions, whether designed to be permanent or removable.

Tissue anchoring element 12 can be fabricated from any material including metals, alloys, polymers and the like. The structure of anchoring element 12 can be rigid, compliant or elastic in nature. Anchoring element 12 can be constructed from a combination of materials which provide the rigidity necessary for resisting forces applied to the anchor while maintaining a soft non-traumatic interface with the tissue, thereby minimizing tissue abrasion. For example, a t-bar anchoring element 12 can be constructed by over-molding a rigid plastic or metal bar or wire with silicone to form a T which has a silicone covered cross bar and a silicone tether stem. The use of over-molded metal also provides anchoring element 12 with radio-opacity and thus enables identification thereof using imaging techniques. Alternatively part or all of anchor 10 and/or device body 152 can include a radio-opaque material such as barium sulfate.

The loading capabilities of anchoring element 12 are determined by a combination of structure, size and choice of materials. It will be appreciated that such loading capabilities can be designed into anchoring element 12 according to use and site of anchoring.

As used herein, the phrases "elastic properties" or "elastic compliance" are used interchangeably to refer to the ability of tether 14 or a portion thereof to reversibly increase in length under a pulling force. Such an increase in length can be at least 10%, preferably at least 25%, more preferably at least 50%. The elastic properties of tether 14 can be provided by the tether structure, cross sectional and axial geometries and/or tether material. A non-elastic tether can have functional elastic properties if the tissue is allowed to ride on the axis of the tether unconstrained and/or if device body 152 is biased against the tissue using a spring mechanism, such as spring element 36 in FIG. 1g. Functionally, an elastic tether provides minimum or a controlled resistance to tissue motion.

Tether 14 can be a hollow or solid thread or string-like structure which includes one or several adjoined portions. Tether 14 can be made out of a twisted or braided set of smaller elastic filaments, much like a bungee cord. Such a braided design will allow cell ingrowth and better integration into the host tissue. A tether 14 constructed from two adjoined portions can be used to provide a unique elastic profile, wherein one portion elastically stretches and another does not, or where both portion stretch, each to a different degree. A multi-portion tether configuration can also be used to simplify construction of anchor 10 of the present invention. For example, anchoring element 12 and a first portion of tether 14 can be molded from a single material and attached to a second and elastic portion of tether 14 via gluing, press fit, over-molding and the like. A multi-portion tether 14 configuration can also be used in cases where different portion are exposed to different environments, for example, when a first portion of tether 14 resides within a tissue and another in a lumen. Tether material can be inelastic and yet tether 14 can be configured to provide elasticity, e.g. an elastic coil structure. For example, tether 14 can be inelastic and be wound around a rotary-spring-loaded drum in the device body, or is attached to an elastic structure disposed under device body 152 to allow for an elastic effect with inelastic tether materials.

Tether 14 can also include a stopper 20 structure for limiting movement of tether 14 and anchoring element 12 in an unwanted direction. Such a stopper 20 can be thickening of tether 14, a disc disposed on tether 14, or a barb or other protrusion.

Figure 1D:
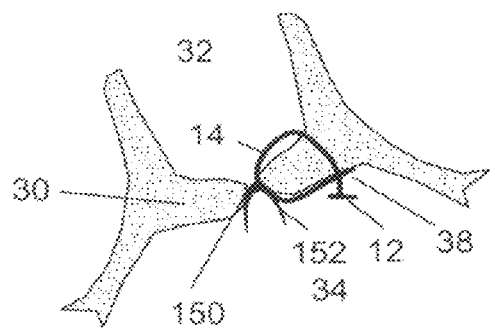

Device body 152 can also be anchored to the wall of the stomach or esophagus using an anchor 10 which does not include an exposed length of tether 14. For example, a semi-rigid flap configuration of device body 152 can be anchored right under the LES. Such a configuration can be hinged on one side and anchored directly at the hinge to the stomach wall adjacent to the LES as depicted in FIG. 1e.

Device 150 depicted in FIG. 1a is designed to suspend from the site of anchoring within the LES or preferably a distance of zero to several centimeters above or below the Z line or squamocolumnar junction of the LES, thereby not preventing passage of food during swallowing and thus not inducing dysphagia. However, when reflux occurs, the force of the refluxing acid and/or the force of an elastic tether 14 biases device body 152 (which is suspended within the path of reflux) against the lower side of the LES thereby preventing acid reflux through the LES and into the esophagus. Device body 152 is sized and of proper mechanical composition to resist being pushed up through the LES into the esophagus during normal physiological conditions, including during a reflux episode. The length of tether 14 of anchor 10 and the site of attachment of tether 14 to device body 152 can be predetermined and/or adjusted following implantation of device 150 in order to ensure correct suspension of device 150. To that effect, it is possible to separate the procedure into two parts: the implantation of anchored tether 14 with a free end, and then separately the suspension of device body 152 on tether 14 at the appropriate position.

To enable a subject to release gas from the stomach and to vomit if need be, device body 152 can be sized small enough such that gas is forced up the side of the stomach and esophagus tissue without being blocked by device body 152 while still remaining tethered. Alternatively, at least a portion of device body 152 opens or buckles under pressures exerted by vomiting fluids or gasses (e.g. device body 152 can be configured with a split, leaf or flap valve which opens under predetermined backflow pressures). It is also possible that gas can escape around device body 152 by peeling it away transiently from the tissue surface. Alternatively, device body 152 can be large and stiff enough to prevent being pushed up the esophagus during vomiting and therefore effectively block vomiting.

Figure 1B:
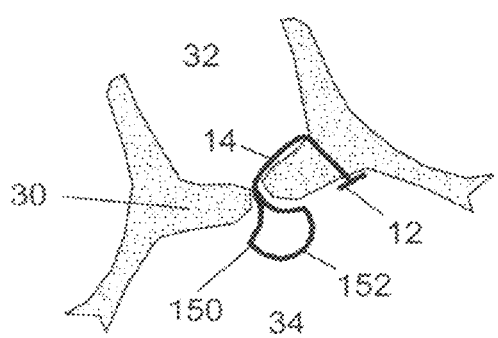
Figure 1E:
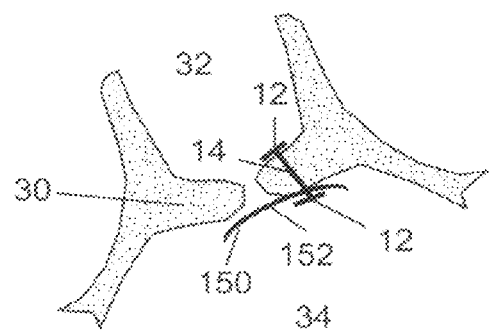

FIG. 1b illustrates another embodiment of device 150. In this embodiment, device body 152 is shaped as a solid ball or hollow balloon having a volume of 0.1-10 cm$^3$ filled with a solid (e.g. silicone), gel (e.g. silicone gel), gas (e.g. air) or a liquid (e.g. saline). A balloon configuration of device body 152 can function as a tethered float which can float on top of the front of the refluxing acid to block the LES and prevent acid leakage into the esophagus.

Anchoring configuration of such a balloon device 150 can be as described for FIG. 1a. An alternative anchoring configuration uses single or multiple anchoring points of the balloon device in the upper portion of the stomach adjacent to the LES using a retroflexed endoscope for example. As long as the tether is properly sized, device body 152 will be close enough to the LES to effectively seal it during reflux without necessarily being in contact with the LES on a constant basis. Typical tether 14 lengths can be 0-10 cm, preferably 0.1-2 cm. Device body 152 can be adjustably inflated/deflated or filled/emptied with a gas or fluid after implantation via endoscopic means using a septum or other valve as described later.

Figure 1C:
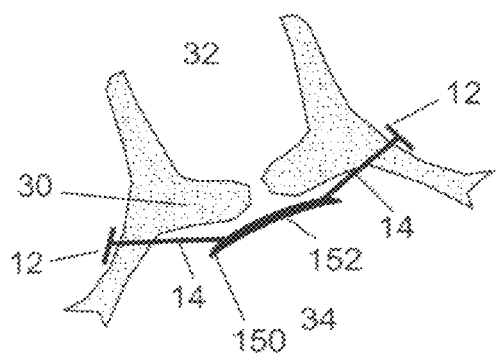

FIG. 1c illustrates another embodiment of device 150. In this embodiment, device body 152 is a thin flat sheet suspended underneath LES 30 by two or more tethers 14 and two or more anchoring elements 12 anchored in or through the wall of stomach 34. In this embodiment, device 150 forms a "trampoline" underneath the LES and seals when the pressure in stomach 34 is greater than the pressure in esophagus 32, i.e. during reflux.

In an alternative anchoring embodiment, device 150 is anchored to anchoring element 12 which is placed under the submucosa of the esophagus much like the bulking elements of the Medtronic Gatekeeper™ bulking device. Tether 14 emerges through a hole in the submucosa and attaches to device body 152. In this embodiment, no muscle is penetrated. Device 150 can also include configurations which are suitable for treating GERD cases caused by or exacerbated by Hiatal hernias (diaphragmatic hernias). Hiatal hernia is a condition in which the upper portion of the stomach protrudes into the chest cavity through an opening of the diaphragm (esophageal hiatus). Weakening and enlargement of this opening facilitates upward passage or even entrapment of the upper stomach above the diaphragm which leads to increased acid reflux into the esophagus.

To prevent or at least partially correct any tissue deformation caused by such hernias, device 150 can also include a stopper positioned along the length of tether 14 above device body 152 (or else device body 152 itself can act as the stopper) to lodge in the LES and by increasing its effective diameter prevent the esophagus from moving up through the herniated diaphragm.

Figure 1F:
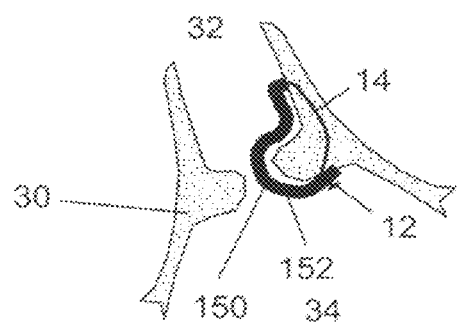
Figure 1G:
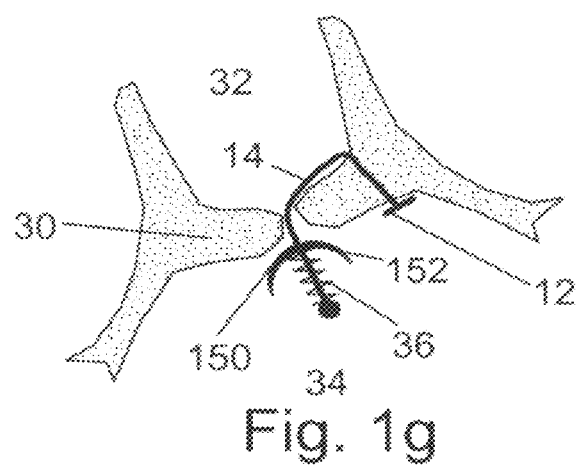
Figure 1H:
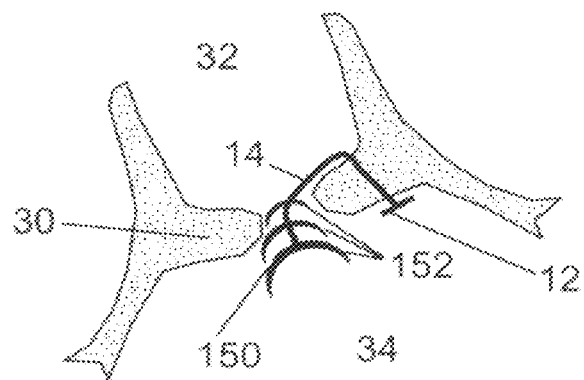

In an alternative embodiment, device 150 can include more than one device body 152 which can be stacked like discs on a single tether 14 to seal at various heights in the esophagus (FIG. 1h). Such a configuration can be especially advantageous in hiatal hernias as the actual LES can be above the effective sphincter formed by the diaphragm muscles and there is a need to seal at various levels of the passageway between the stomach and the esophagus. If three sequential seals each block only 90% of the reflux, the effective blockage rate is 99.9%. Likewise an 80% block at each seal still leads to approximately 99% of total reflux block.

Figure 5A:
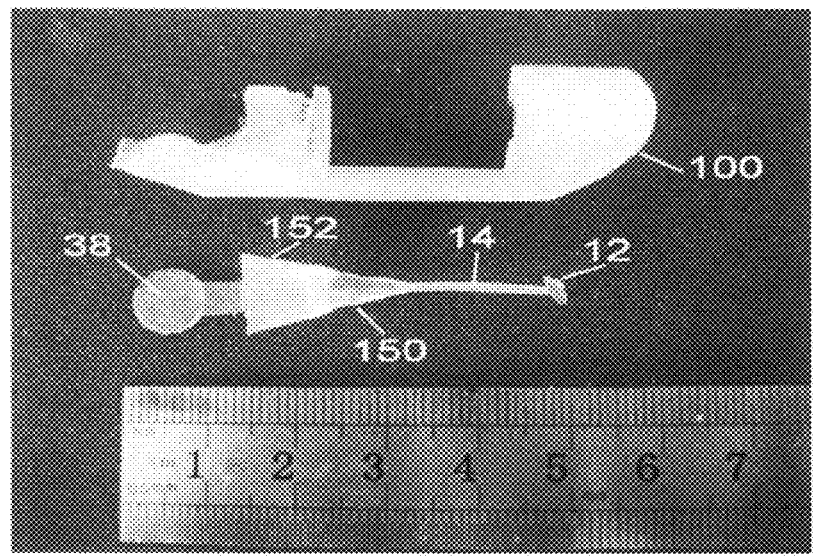
FIG. 5a-b illustrates a GERD treatment device and delivery device constructed according to the teachings of the present invention.

In an alternative embodiment, illustrated in FIGS. 1d and 5a, device body 152 is secured to the distal end of tether 14 by having anchoring element 12 penetrate a washer region 38 or separate portion of device body 152 and bias it against the wall of the LES. An advantage of this approach is to limit the stretching of tether 14 by peristaltic waves in the GI system by biasing device body against the side of the lumen. Furthermore, upward displacement of device body 152 due to reflux flow or a higher stomach pressure is minimized by the resistance to motion of the bottom anchoring. Washer region 38 can be attached to device body 152 via an elastic member to form one contiguous device 150, or washer region can be completely separate from device body 152 and held in place by the delivery head (as pictured in FIG. 5b), which is then penetrated by anchoring element 12 during the implantation process. The role of washer region 38 is to distribute the load of anchoring element 12 on the wall of the tissue in order to prevent anchoring element 12 from eroding or burrowing into tissue due to long term pressure, thereby making device removal easier as only tether 14 runs through the tissue.

In a further embodiment, illustrated in FIG. 1e, device body 152 is anchored underneath the LES using a separate tether 14 with two anchoring elements 12. An advantage of this embodiment is that the downward pull of peristaltic forces does not cause the top portion of tether 14 to cut into the esophageal tissue.

In yet a further embodiment, illustrated in FIG. 1f, device body 152 is anchored like the embodiment in FIG. 1d, but in this case device body 152 acts as an internal bulking agent within the esophageal lumen. Device body 152 forms a mandrel or solid surface around which the LES can seal.

In yet a further embodiment, illustrated in FIG. 1g, tether 14 is inelastic (for example a 2-0 polypropylene suture) and device body 152 is free to slide along it. The functional elasticity in the system is provided by a low profile spring element 36 which biases device body 152 up against the LES.

In yet a further embodiment, illustrated in FIG. 1h, tether 14 is attached to a plurality of device bodies 152, so that no matter where the exact sealing region of the LES is along tether 14, at least one device body 152 will be near the minimum opening of the LES and therefore will facilitate maximum augmentation of the sealing function.

Device 150 can be configured using full or partial combinations of the individual features described in the embodiments of FIGS. 1a-h.

Preferably, device 150 in its entirety, including device body 152 is sized so that in the case of detachment from the anchoring tissue, device 150 passes through the pylorus and is harmlessly passed through the GI system.

Additional embodiments of device 150 can employ device body configurations which employ flap or other valve-like structures (which can be anchored by 2 or more anchoring devices), one or more flaps which are directly anchored to the wall of the stomach adjacent to the LES with their free end(s) extending underneath the LES opening and fluid filled bodies which float above stomach acid. Device body configuration which change configuration when exposed to acid (e.g. an acid sensitive polymer mesh that seal when exposed to acid or an acid sensitive polymer strip that balls up when exposed to acid) are also envisaged herein. Such device bodies can be fabricated from, for example, porous lightly crosslinked diethanolamine derivatized poly(vinylbenzyl chloride) which can be toughened with Kraton G1652 or styrene-ethylene, butylene-styrene triblock copolymer. Also contemplated are device bodies composed of loose brush-like or tentacle-like strips that when at neutral pH allow gas to go through but when acidic or physically squished together under pressure effectively block fluid flow, and device bodies which include in-situ gelling or curing substances which can be molded into the space within or below the LES to form a custom-fit configuration which can be attached to the anchor during the molding process or thereafter (for example vinyl polysiloxane impression material). In this manner, device body 152 receives the exact shape of the opening of the LES lumen which is the defect that allows for reflux. Device 150 can have device body 152 made from a soft material (e.g. shore A hardness 10 or less) or an open-cell or closed-cell sponge material (example materials include silicone, polyurethane, PTFE, etc) that allow for device body 152 to conform exactly or approximately to the anatomy of the LES and not allow the passage of acid upwards. Device 150 can have device body 152 made from a relatively hard material (such as plastic, glass, ceramic or metal) that will cause the LES tissue to deform and conform the shape of device body 152. Another example of a device body 152 configuration comprises an ultra-thin membrane (less than 1 mm) of an acid-resistant material.

It will be appreciated that custom fitted device bodies can also be utilized in which case a non-elastic sizing balloon is first utilized to measure the inner ID and pressure of the LES region and the size and geometry of the anti-reflux device body is selected accordingly. Device 150 can be configured such that device body 152 can be easily replaced periodically if need be. Such replacement can be facilitated via use of a detachable device body-tether coupler (e.g. hook and loop). Such a modular configuration of device 150 enables replacement of device body 152 in cases of erosion or damage to device body or in cases where a different size/shape/location of device body 152 is needed.

Device 150 of the present invention can be anchored to the wall of the stomach or esophagus using any appropriate surgical technique. Preferably, device 150 is anchored using an endoscopic delivery apparatus which is present in the esophagus above the LES for viewing the insertion of the needle into the esophagus and also a rearward curving visualization means pushed through a separate working channel into the stomach to view the position of the delivery cup relative to the LES sequentially or simultaneously (see for example the Avantis Third Eye Retroscope™—avantismedical.com)

Anchoring using an endoscopic approach can be effected as follows. Device 150 can be loaded onto a delivery rod or endoscope fitted with a delivery head which is configured capable of delivering anchoring element 12 and attached tether 14 into or through a wall of the esophagus, stomach, or LES (see for examples FIGS. 5a-b).

The delivery head and loaded device 150 are inserted through the mouth of an anesthetized or sedated subject and into the esophagus and advanced to the point of the LES. Optionally, a separate endoscope or a backward-looking scope or camera (delivered alongside or through a working channel of the endoscope) is lowered into the stomach and retroflexed to sight the position of the delivery head relative to the LES.

Alternatively, the delivery head can be fitted on the outside surface of an endoscope having a retroflexible camera head. For example, the delivery head can be fitted on the endoscope (e.g. a GIF-N180 "babyscope" of 4.9 mm diameter) as a slidable and rotatable cuff running the length of the endoscope. Such a configuration can be used to deliver device 150 to the desired tissue region while using the camera of the endoscope to view the LES in a retroflexed maneuver from the stomach looking up to maneuver the cuff and thereby position the delivery head of the device right at the desired position (the Z line for example) before executing the actual device delivery.

In an alternative embodiment, the delivery head can be mounted on a hollow tube or delivery rod which is first introduced into the esophagus, and then a normal or a 'baby endoscope' is inserted through this tube and retroflexed to view the position of the delivery head from below as per the example above.

In yet a further embodiment, the delivery head can be mounted on a delivery device tube or rod and introduced into the esophagus without visualization. A normal or baby endoscope can be introduced in parallel to the delivery device to view the implantation site en face and or in a retroflexed manner. A handle on the proximal end of the delivery device tube or rod is used to adjust the desired location of the delivery head relative to the LES both axially and rotationally as described above under direct visualization. A vacuum can then be delivered through the delivery device tube or rod along at least one portion of its length to affix the device delivery tube to the esophagus. The normal or baby endoscope can then be removed from the esophagus so that it is not distending the LES while the vacuum affixes the device delivery head to the implantation site and prevents any motion during endoscope withdrawal. Then a second vacuum source can be activated to suck tissue into the vacuum cup of the delivery head in preparation for device implantation. The depth of the vacuum cup determines the depth of anchoring (1-7 mm being the preferred depth in order to reach into or beyond the muscle layer) and the length of the vacuum cup determines the path length of the tether through the tissue (5-30 mm being the preferred path length). Assuming that the delivery head is low profile (10 mm or less at its maximum diameter), the embodiment described above allows implantation during a minimum distention of the LES and closest to its relaxed and closed position.

The delivery head can be slightly angled or be angleable relative to the delivery tube or rod used to push it in to the esophagus to allow the distal tip of delivery head with its vacuum cup or LES invagination space, to better follow the outward curvature of the tissue in the region of the LES. Such angulation can be built into the natural shape and form of the delivery system, or controlled by the operator.

The delivery head can be utilized to deliver anchor 10 of device 150 through the upper portion of the LES, and out of the lower portion of the LES; anchoring element 12 (e.g. t-bar) is then secured against the lower wall of LES thickening, with or without a washer region 38. Alternatively, anchoring element 12 is delivered outside the GI tract and juxtaposed against the serosa. In any case, once anchoring element 12 is deployed, device body 152 is released within the stomach and the length of tether 14 (and possibly point of attachment to device body 152) is adjusted if necessary such that device body 152 resides just below the LES and in the patch of reflux. The delivery apparatus can then be removed from the subject. Delivery apparatus 100 can contain more than one anchoring element 12 if they are stacked end to end inside the inner lumen of delivery device. In this fashion, it is not necessary to remove and reload the endoscope with a separate anchor 10 for each tether 14 attached to device body 152. A threaded advancement pushrod mechanism, for example, inside the delivery head can be used to controllably deploy each anchoring element 12 separately.

As is mentioned above, device 150 can be implanted in a modular manner. Anchoring element 12 and tether 14 can be implanted and then device body 152 can be attached to tether 14 at a suitable position in a separate procedure. Device body 152 can be removed and/or interchanged through minimally invasive means with a device body 152 having a different size and/or shape without requiring a new anchoring procedure. Device body 152 can be adjustably mounted on tether 14 to allow repositioning of device body 152 after initial positioning.

In the implantation procedure, ultrasound can be used prior, during or after implantation to verify the depth of tissue at which anchoring occurred or should occur, and the delivery method modified or verified appropriately. Furthermore, it is possible to inject contrast agent through the delivery needle and image it in real time before deploying the anchor to verify that none of the contrast agent escaped into the chest or peritoneal cavities, indicating that the implantation path did not cross outside of the LES and esophageal tissue. In cases where the implantation path does cross outside the GI tissue, implantation can be aborted or modified.

In a further embodiment, device body 152 can be hollow and adjustable in size based on the injection of a fluid, gas or gel. In this embodiment, device body 152 can be filled by engaging it with vacuum means to the end of an endoscope (using a small distally mounted vacuum cup) to provide counter force to a delivery needle that is used to puncture a septum in device body 152 through which the fluid, gas or gel is introduced.

Figure 3A:
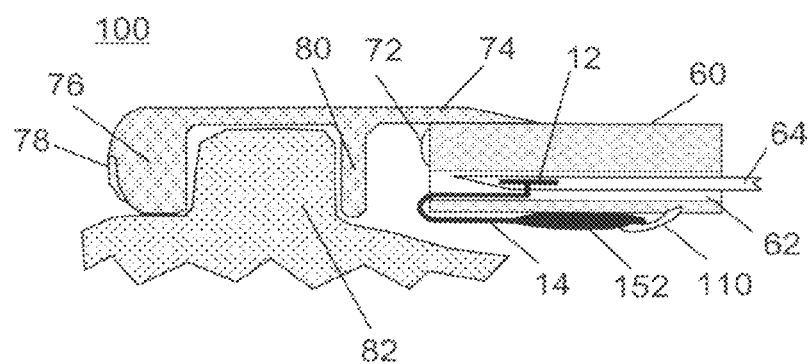
FIGS. 3a-c illustrate an apparatus for delivering and positioning a device constructed in accordance with the teachings of the present invention.
Figure 3B:
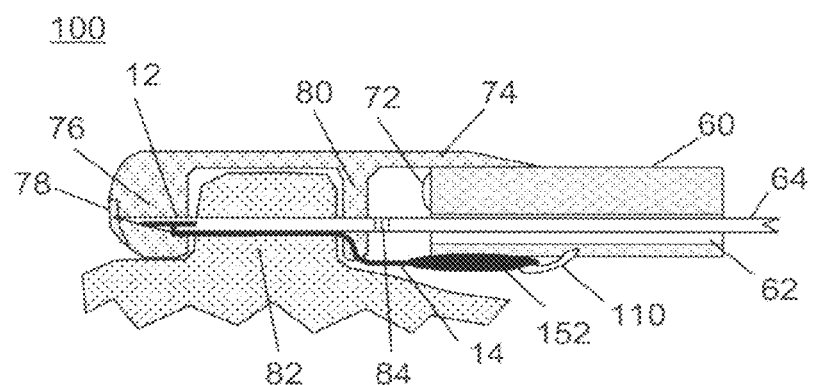
Figure 3C:
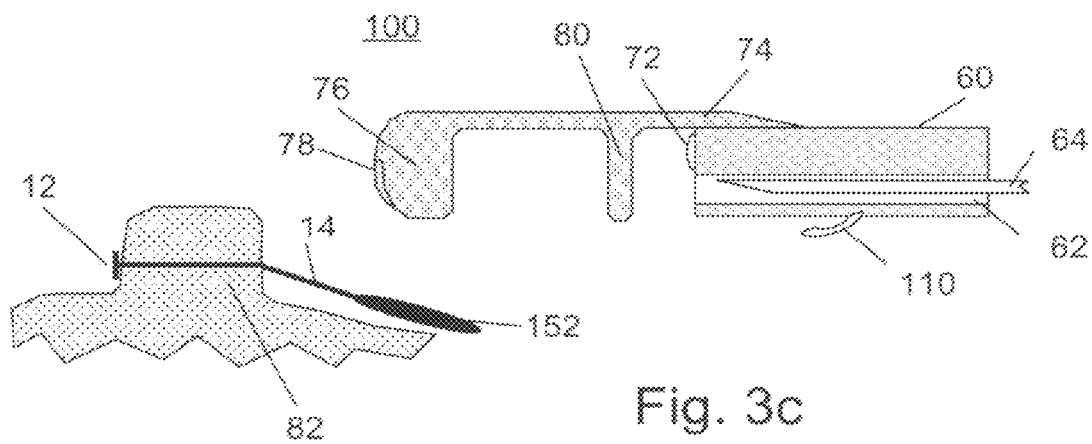

FIGS. 3a-c illustrate an apparatus and method for delivering and anchoring device 150 which is referred to herein as apparatus 100. Apparatus 100 includes an endoscope 60 (only distal tip shown) having one or more working channels 62 and preferably a camera 72 and/or a camera which can curve back) (~180° out of a separate endoscope working channel.

Apparatus 100 includes a delivery device 64 (needle configuration shown In FIGS. 3a-c) which functions in carrying anchoring element 12 and delivering it through GI wall tissue. Delivery device 64 is deployed and operated through working channel 62. When shaped as a needle, delivery device 64 can be constructed such that when sequestered within the working channel of an endoscope it does not substantially prevent bending of the working tip of an endoscope. This can be achieved by using a short needle (e.g. 10 mm) attached to a flexible pushrod or by fabricating the needle from an elastic alloy such as Nitinol. Apparatus 100 further includes an optional delivery head 74 which is mountable on distal end of endoscope 60.

Delivery head 74 has several functions. First, it allows the operator of apparatus 100 to see the path that delivery device 64 will take when pushed out or working channel 62. Second, it prevents delivery device 64 from unwanted perforation of the lumen. Third, it provides a positioning aid and control over the depth and length of the insertion path for anchoring element 12 and tether 14 through tissue 82 enabling positioning of device 150 at a known distance from the opening of the LES. Fourth it provides a force which counteracts the pushing of delivery device 64 given the endoscope 60 may not be rigid enough to resist such a pushing force without moving and therefore losing the control and alignment of the insertion path of anchoring 12 and tether 14 into tissue 82.

Delivery head 74 is optionally transparent so as to not interfere with the operator's field of view as viewed through camera 72. Delivery head 74 is also designed to easily enter a sphincter and fit, in a delivery position, against sphincter tissue. For example, delivery head 74 can have a distal 76 and optionally a proximal 80 protrusion that can be used to position delivery head around the ridge of the LES. Delivery head 74 can be positioned against tissue 82 passively using the twisting and axial positioning of endoscope 60 along with manipulation of the alignment wheels of endoscope 60 and/or through vacuum provided by a vacuum chamber in the delivery head. Other tissue approximation approaches such as pullable helical or temporary anchors connected to alignment head between distal arm 76 and proximal arm 80 are also envisaged herein. The distance between distal 76 and proximal 80 protrusions determines the path length of delivery device 64 in tissue 82. Likewise, the height of these protrusions determines the depth of insertion of tether 14 into the tissue of interest. A short depth (e.g. short arms of approximately 2-4 mm) would allow for sub-mucosal anchoring while greater depth (e.g. long arms of approximately 5 mm or more) would allow for anchoring through muscle or even penetration outside the serosa. The importance of the proximal protrusion 80 is that the entry point of delivery device 64 into the tissue can be visualized by camera 72 until delivery device 64 either hits needle stop 78 or marker 84 on delivery device 64 is aligned with proximal arm 80 (see FIG. 3b). Without proximal arm 80, tissue 82 can press up against camera 72 and the operator of apparatus 100 may not be able to visualize the insertion point of delivery device 64. All parts of alignment head 74 are atraumatic with rounded corners and optionally flexible side to side to prevent tissue damage while being manipulated in the GI lumen. Examples of suitable materials for alignment head 74 is molded plastic or silicone covered metal wire.

Device 150 (made up of anchoring element 12 tether 14 and device body 152) can be pulled along the outside of endoscope 60 from outside the body through the mouth and esophagus into the region of interest using a friction fit between anchoring element 12 and the delivery device 64. Lubricant such as KY can be used to minimize friction of endoscope 60 and device 150 through the passageway to the implantation site. Apparatus 100 optionally includes an element 110 for securing device 150 to endoscope 60. Although device 150 can be introduced into the stomach separately from the introduction of endoscope 60, using endoscope 60 to carry device 150 into the stomach is preferred. Element 110 can be a passive deflector that shields device 150 from the friction of the sliding of the delivery head in the esophagus or an active snare or sheath which is deployable from working channel 62, an alternative working channel or actuator means running alongside endoscope 60. For example, a snare configuration can be realized by looping a wire out of channel 62. Such a loop can be pulled from proximal end of endoscope 60 through holes around the outside of a cup placed on the distal end of endoscope 60 (such cups are used for polyp snares and band ligation for example) and used to secure (ensnare) tether 14 or device 150 against the body of endoscope 60 or the distal cup attached thereto. Once anchoring element 12 of device 150 is delivered by delivery device 64, element 110 can be released to release device 150 from apparatus 100.

With reference to FIGS. 3a-c, in a typical procedure alignment head 74 of apparatus 100 is positioned around the ridge of tissue 82 as in FIG. 3a. Delivery device 64 is pushed through tissue 82 until reaching needle stop 78 or until marker 84 is aligned with proximal arm 80 as viewed by camera 72 as in FIG. 3b. Anchoring element 12 is pushed out of delivery device 64 using a flexible pushrod (not shown) running along the inside lumen of delivery device 64 operated at the proximal end of endoscope 60. Delivery device 64 is withdrawn back into working channel 62 of endoscope 60 and apparatus 100 is removed from the patient leaving device 150 anchored in tissue 82 as in FIG. 3c. Device 150 can be removed by cutting tether 14 at either end of where tether 14 emerges from tissue 82. The remaining portion of tether 14 and anchoring element 12 can either be pulled out using endoscopic means or left to extrude out of the tissue and pass harmlessly through the GI tract.

Device 150 can also be delivered and anchored using a suturing laparoscope (e.g. the Wilson Cook ESD) onto which device 150 is loaded. Optionally, the procedure can be viewed using direct visual guidance from a separate endoscope that is inserted in parallel to the laparoscope in order to view the insertion and exit points of the delivery device 64.

In an alternative embodiment, device 150 can be in the form of a short (e.g. 5-10 mm relaxed length) elastic tether with two anchors that plicate the tissue of the LES, both anchors residing against the inside surface of the GI lumen and the elastic tether going through the submucosa and muscle. In this manner, the elastic tether can provide sufficient force to plicate the tissue and augment the LES or change the angles or neighboring tissues to increase LES sealing, yet also being capable of expanding when the LES dilates during food ingestion so as to not tear through the tissue or cause tissue erosion as one gets when using a non-compliant suture material. In treating GERD, one or more such devices can be used in a circumferential manner around the LES region. Alternatively, the compliant tether can be sewn in a zig zag manner in the LES tissue around its circumference, properly tensioned and terminated at both ends with an anchor element, thereby providing an elastic circumferential compressive force to help close the LES and prevent reflux. The tether in this embodiment may be flat, like a ribbon, to minimize intrusion into the esophagus.

In an alternative embodiment, a patient can receive both an anti reflux device and a gastric implant for modifying eating behavior attached through a common anchor to the LES and both device bodies attached at different locations along a single tether as one integrated or modular device.

In a further embodiment, device body 152 can be tethered right under the LES using a long, thin and flexible tether running up the esophagus all the way up to the region of the oropharynx or nasopharynx (for example clipping it to a tooth, an oral appliance or the cartilage/bone forming the nasal septum). Tension could be adjusted on tether 14 to keep device body 152 up against the LES with a gentle pressure, yet elastically tethered to the point of having device body 152 move a bit with the food or peristaltic waves, yet return to its original position once the food or peristaltic wave has passed. This could be a temporary anchoring to determine if the patient will benefit from such a device being permanently implanted, or it could be the permanent method of anchoring. It is believed that if the tether is thin and elastic enough (e.g. 0.5-1.5 mm diameter silicone thread), its presence will not be felt in the esophagus. The advantage of such an anchoring configuration is the lack of a needle puncture in the region of the LES. Furthermore, the device, once attached to the upper anchoring point, can simply be swallowed as the means of delivery. Peristalsis will try to pull device body 152 deeper into the stomach, and the elastic tether will apply gently counter force to keep it on the underside of the LES, thereby reducing reflux.

Figure 4A:
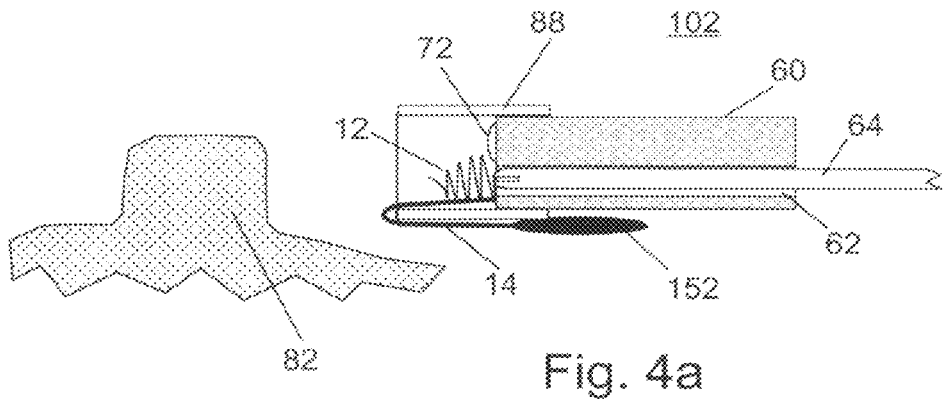
FIGS. 4a-c illustrate an alternative embodiment of an apparatus for delivering and positioning a device constructed in accordance with the teachings of the present invention.
Figure 4B:
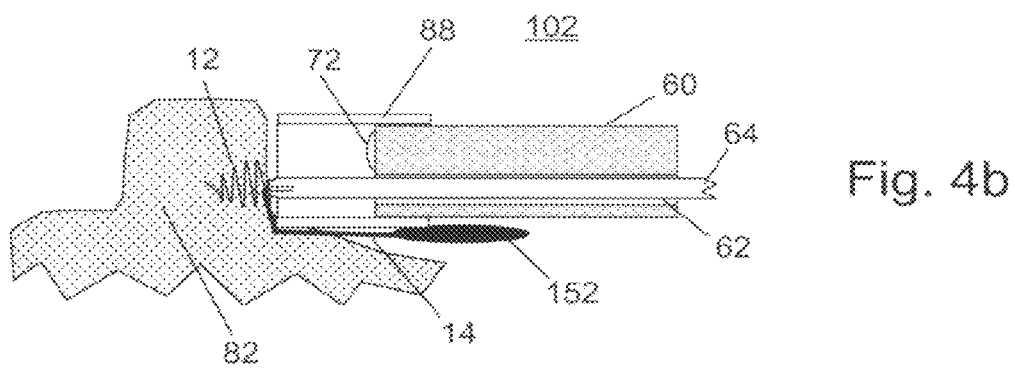
Figure 4C:
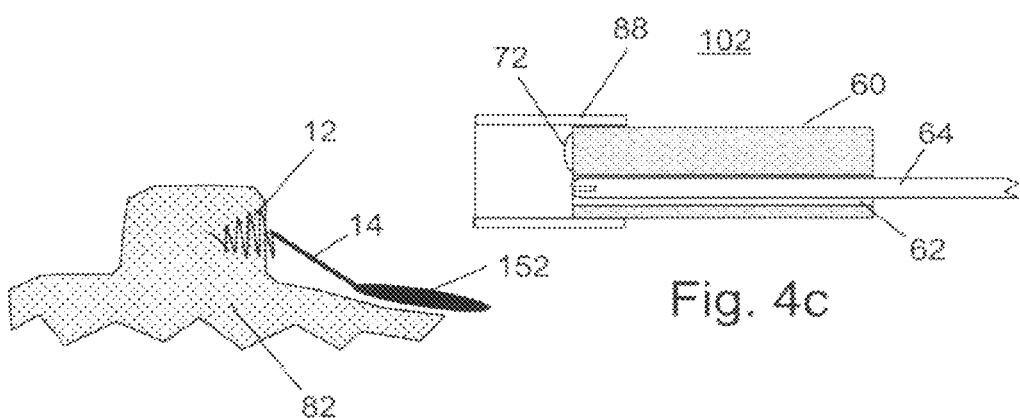

An alternative anchoring scheme is shown in FIGS. 4a-c. The procedure shown in these Figures illustrates anchoring of device body 152 to GI tissue using a cork screw anchoring element 12. In such a configuration delivery device 64 is preloaded with anchoring element 12 and is delivered straight into the tissue optionally while being torqued. The cork screw anchoring element 12 is inserted or torqued into submucosal or preferably muscle tissue and is retained via its helical coils.

Delivery of a GERD device of the present invention to the LES of an animal subject is further described in Examples 1-2 which follow.

It will be appreciated that device 150 can also be used to intermittently block other sphincters and orifices in the body. For example, device 150 can be used in gastritis patients to intermittently block bile reflux from the duodenum to the antrum. For such purpose, the present device is configured for pyloric sphincter anchoring and the tether length and device body size and shape are selected accordingly.

Device 150 can also be configured for use in intermittently blocking reflux of urine from the bladder into the ureter, a condition known as vesicoureteral reflux (VUR). Urine normally flows in one direction—down from the kidneys, through tubes called ureters, to the bladder. VUR is the abnormal flow of urine from the bladder back into the ureters. VUR can lead to infection because urine that remains in the urinary tract provides a place for bacteria to grow. In this application, device body 152 sits inside the bladder below the ureter/bladder junction and prevents urine from flowing back up into the ureters.

The present device can also be configured for preventing bile reflux through the papilla of Vater. Such a configuration of the present device can include an umbrella-shaped device body attached via a 0.2-1 cm long tether to the wall of the small intestine or the bile duct.

The devices described in this patent application can be provided as a kit with or without an endoscope and camera. The devices and kits can be pre-sized for various patient populations, from infants up to large morbidly obese individuals, or for individuals with only transient LES relaxation to major openings of the LES as occurs in Barrett's esophagus for example.

As used herein the term "about" refers to +/31 10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following example, which together with the above descriptions, illustrates the invention in a non limiting fashion.

Example 1

Implantation of a GERD Treatment Device

A GERD treatment device and delivery apparatus was constructed and operated ex-vivo on pig stomach-esophagus explants. The device included an anchor (metallic t-bar anchoring element and braided nylon tether) attached to a device body which was fabricated from silicone as a cone attached on top of a flexible sheath (brimmed cone configuration). The delivery apparatus included a standard gastroscope fitted with a hollow delivery needle for carrying the anchoring element (t-bar), and a push wire (plunger) for ejecting the anchoring element from the hollow needle.

The device was loaded onto the delivery apparatus and the delivery end of the delivery apparatus was advanced through the esophagus until the end of the esophagus was reached.

The delivery apparatus was directed to the side of the esophagus and the delivery needle (carrying the t-bar anchoring element) was extended from the working channel and pushed through the top portion of the lower esophageal sphincter (LES), through the LES muscle and into the stomach. The push wire plunger was then operated to eject and release the t-bar anchoring element from the needle. Following release of the anchoring element, the delivery apparatus was retracted leaving a tethered device body anchored to the side of the LES. The device body was then positioned within the stomach, suspended below the LES.

Such a configuration allows food and liquid to freely pass from the esophagus to the stomach. However, during an acid reflux episode, the anti-reflux device is pushed upward by refluxing fluids thereby contacting the lower portion of the LES and sealing, at least partially any opening present between the stomach and esophagus.

Example 2

Implantation of an Anti-GERD Device in Live Pigs

A similar endoscopic delivery apparatus used in example 1 above was used to deliver and anchor the anti-GERD device of the present invention in two adult female pigs (FIGS. 5a-b and 6a-b).

The delivery apparatus employed a 16 gauge slotted needle for delivering the device and an alignment head for guiding the trajectory of the needle through the tissue (see text referring to FIGS. 3a-c for further description). The needle was delivered through a working channel of a standard endoscope (Olympus GIF 130) while the alignment head was mounted on the tip of the endoscope.

Figure 5B:
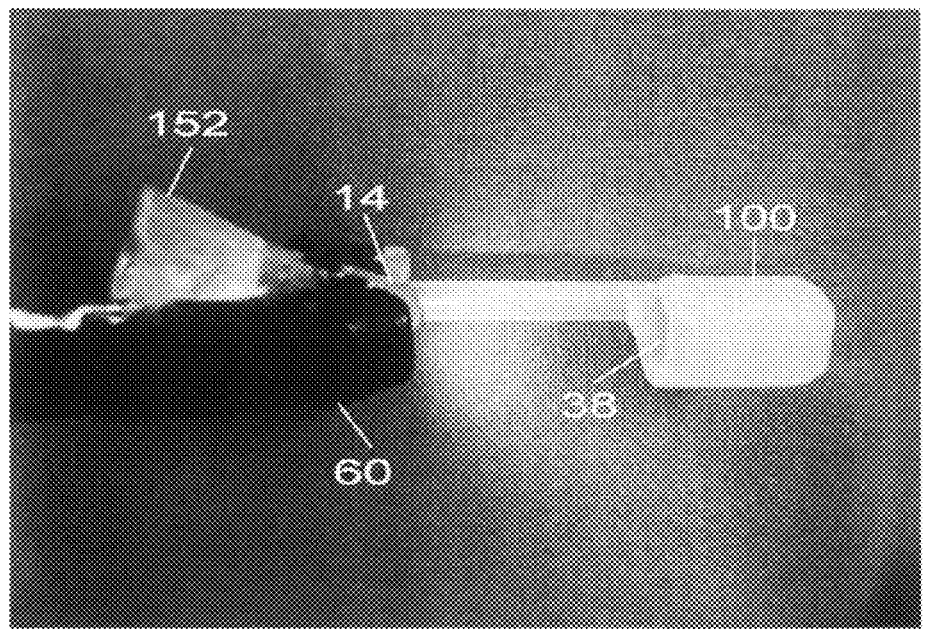

The anchoring element of both devices was a cylindrically-shaped T anchor made from silicone overmolded onto a metal element which is 6 mm long and 1 mm in diameter; the T anchor was inserted into the slotted needle (which was fitted with a wire plunger). The tether was 1 mm diameter silicone and the device body was a hollow silicone cone with an element that formed a washer region for the t-anchor in a closed loop configuration (see FIGS. 5a and 5b, which is also the configuration described in FIG. 1d). In FIG. 5a, device body 152 is attached as one piece to washer region 38 which is mounted in delivery apparatus 100. In FIG. 5b, washer region 38 is separate element that is held in place by delivery apparatus 100 which is mounted on endoscope 60. The device body was attached to the outside of the endoscope using a weak silicone tape that was removable by the operator. The combined delivery apparatus-device was introduced through the mouth of the pigs and into the esophagus.

Figure 6A:
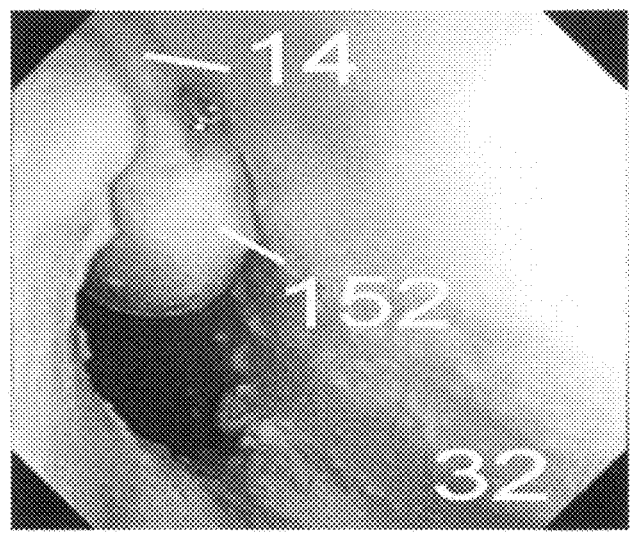
FIG. 6a-b illustrates the anti-reflux device delivered into the stomach of a live pig from the top (in the esophagus looking down) and bottom (in the stomach looking up) views.
Figure 6B:
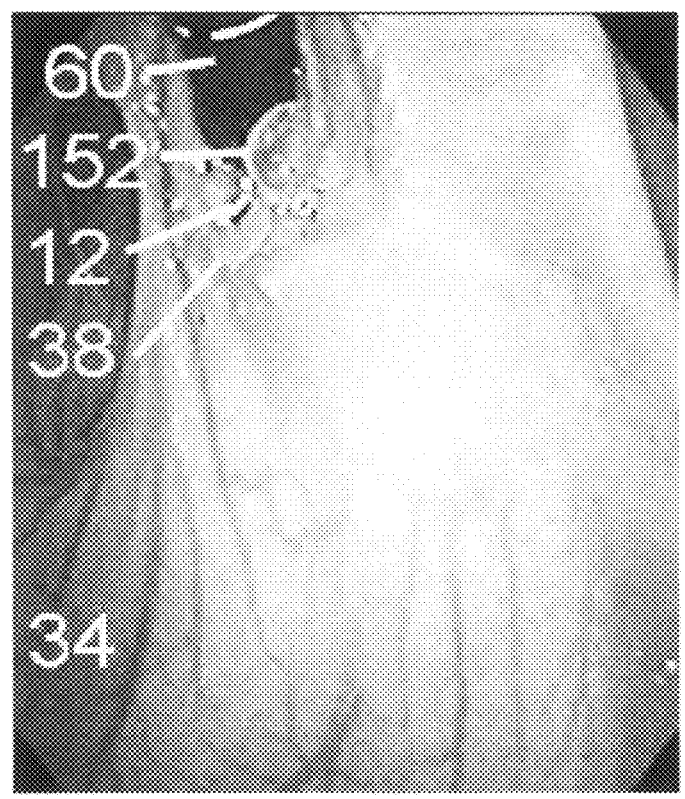

The endoscope was advanced until the alignment head reached the stomach; it was then pushed sideways against the esophagus wall. The endoscope was then gently retracted until the alignment head started pulling up the bottom surface of the LES, which invaginated into the space between the distal end of the alignment head and the distal tip of the endoscope. The needle was advanced until it penetrated the washer region appendage of the device body and entered the hollow distal portion of the delivery head. The push wire plunger was then operated to eject and release the t-bar anchoring element from the needle. The needle was retracted and the endoscope was gently removed. As a follow up check, the same GIF 130 endoscope without the alignment head attached was introduced through the esophagus and used to view the device from above (FIG. 6a—note that device body 152 is suspended on tether 14 and is pushed to the side of esophagus 32 by anything traveling down the esophagus) and then further into the stomach and then retroflexed to view the device along with the endoscope itself emerging from the esophagus into the stomach (FIG. 6b). Note how device body 152 is pushed to the side and does not interfere with the passage of endoscope 60 (and therefore any comparable esophageal content) into stomach 34. Anchor element 12 and washer region 38 are also visible in FIG. 6b. The endoscope was then removed from the stomach leaving behind the anti reflux device tethered below the LES. When the esophagus is empty, the tether centers the anti-reflux device in the passageway and prevent the acidic gastric content (yellow liquid on left side of FIG. 6b) from refluxing back into the esophagus. Upon sacrificing one of the two animals, it was noted that no inflammation or irritation of the LES region was noted and that the tether was implanted at a depth of 4 mm, with no inflammation or irritation along the tether's path through the tissue. The second animal was kept alive and at a 3 month follow up the device was intact and still well positioned, with no erosion, inflammation or irritation present in the LES region based on a visual endoscopic examination. It is therefore demonstrated that the valve device of the present invention is stable and unobtrusive in the LES region of a large mammal.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of reducing gastric reflux comprising:
    (a) providing a device having a tether attached to a device body, said device body being configured for preventing reflux while enabling ingested material to flow between said device body and esophageal or stomach tissue and into said stomach; and
    (b) suspending said device body within or below an LES by anchoring said tether to a tissue at or above said LES.

2. The method of claim 1, wherein said device body is sized and shaped for enabling said LES to seal around said device body.

3. The method of claim 1, wherein said tether is elastic.

4. The method of claim 1, wherein said flow of ingested material collapses said device body in an inward radial direction.

* * * * *